US007939257B2

(12) United States Patent
Kwitek et al.

(10) Patent No.: US 7,939,257 B2
(45) Date of Patent: May 10, 2011

(54) POLYMORPHIC GHSR NUCLEIC ACIDS AND USES THEREOF

(75) Inventors: Anne E. Kwitek, Iowa City, IA (US); Andrea Baessler, Sinzing (DE)

(73) Assignee: Third Wave Technologies, Inc., Madison, WI (US)

( * ) Notice: Subject to any disclaimer, the term of this patent is extended or adjusted under 35 U.S.C. 154(b) by 442 days.

(21) Appl. No.: 11/914,326

(22) PCT Filed: May 12, 2006

(86) PCT No.: PCT/US2006/018530
§ 371 (c)(1),
(2), (4) Date: Dec. 22, 2008

(87) PCT Pub. No.: WO2006/124664
PCT Pub. Date: Nov. 23, 2006

(65) Prior Publication Data
US 2009/0215043 A1    Aug. 27, 2009

Related U.S. Application Data

(60) Provisional application No. 60/680,087, filed on May 12, 2005.

(51) Int. Cl.
*C07H 21/04* (2006.01)
*C12Q 1/68* (2006.01)
(52) U.S. Cl. ......... 435/6; 435/91.1; 435/91.2; 536/23.1; 536/24.3
(58) Field of Classification Search .................. None
See application file for complete search history.

(56) References Cited

U.S. PATENT DOCUMENTS

| | | |
|---|---|---|
| 4,873,191 A | 10/1989 | Wagner |
| 5,223,409 A | 6/1993 | Ladner |
| 5,474,796 A | 12/1995 | Brennan |
| 5,538,848 A | 7/1996 | Livak |
| 5,614,396 A | 3/1997 | Bradley |
| 5,719,208 A | 2/1998 | Wideman |
| 5,843,654 A | 12/1998 | Heisler |
| 5,858,659 A | 1/1999 | Sapolsky |
| 5,888,780 A | 3/1999 | Dahlberg |
| 5,919,626 A | 7/1999 | Shi |
| 5,925,525 A | 7/1999 | Fodor |
| 5,952,174 A | 9/1999 | Nikiforov |
| 5,985,551 A | 11/1999 | Brennan |
| 5,985,557 A | 11/1999 | Prudent |
| 5,994,069 A | 11/1999 | Hall |
| 6,001,311 A | 12/1999 | Brennan |
| 6,001,567 A | 12/1999 | Brow |
| 6,001,983 A | 12/1999 | Benner |
| 6,017,696 A | 1/2000 | Heller |
| 6,045,996 A | 4/2000 | Cronin |
| 6,051,380 A | 4/2000 | Sosnowski |
| 6,068,818 A | 5/2000 | Ackley |
| 6,080,912 A | 6/2000 | Bremel |
| 6,709,819 B2 | 3/2004 | Lyamichev |
| 7,303,869 B2 | 12/2007 | Stevens |
| 2003/0082544 A1 | 5/2003 | Fors |
| 2003/0152942 A1 | 8/2003 | Fors |
| 2003/0152971 A1 | 8/2003 | Lyamichev |
| 2004/0014067 A1 | 1/2004 | Lyamichev |
| 2004/0018489 A1 | 1/2004 | Ma |
| 2004/0081652 A1 | 4/2004 | Zack et al. |

FOREIGN PATENT DOCUMENTS

| | | |
|---|---|---|
| WO | WO90/08832 | 8/1990 |
| WO | WO97/27214 | 7/1997 |
| WO | WO98/42873 | 10/1998 |
| WO | WO99/67641 | 12/1999 |
| WO | WO00/39587 | 7/2000 |
| WO | WO 2006124664 A2 | 11/2006 |

OTHER PUBLICATIONS

Wang et al. (J. of Clinical Endocrinology, vol. 89, No. 1, pp. 157-162, 2004).*
Mager et al. (PLos ONE, vol. 3, No. 8, pp. e2941, Aug. 2008).*
Gueorguiev et al. (Obesity, vol. 17, No. 4, pp. 745-754, Apr. 2009).*
Gjesing et al. (PLos ONE, vol. 5, No. 4, pp. E10084, Apr. 2010).*
Allison, et al. "The heritability of body mass index among an international sample of monozygotic twins reared apart" Int J Obes Relat Metab Disord. Jun. 1996; vol. 20(6), pp. 501-506.
Barazzoni, et al. "Hyperleptinemia prevents increased plasma ghrelin concentration during short-term moderate caloric restriction in rats" Gastroenterology, vol. 124, pp. 1188-1192 (2003).
Bradley, et al. "Formation of germ-line chimaeras from embryo-derived teratocarcinoma cell lines" Nature. May 17-23, 1984;309(5965):255-6.
Brinster, et al. "Factors affecting the efficiency of introducing foreign DNA into mice by microinjecting eggs" Proc. Natl. Acad. Sci. USA 82:4438-4442 (1985).
Broglio, et al. "Ghrelin, a natural GH secretagogue produced by the stomach, induces hyperglycemia and reduces insulin secretion in humans" J Clin Endocrinol Metab. Oct. 2001, vol. 86(10), pp. 5083-5086.
Carell, et al. "A Novel Procedure for the Synthesis of Libraries Containing Small Organic Molecules" Angew. Chem. Int. Ed. Engl. vol. 33, pp. 2059-2061 (1994).
Carell, et al. "A Solution-Phase Screening Procedure for the Isolation of Active Compounds from a Library of Molecules" Angew. Chem. Int. Ed. Engl. vol. 33, pp. 2061-2064 (1994).
Carlson, et al. "Additional SNPs and linkage-disequilibrium analyses are necessary for whole-genome association studies in humans" Nat Genet 33:518-521 (2003).
Chamberlin, et al. "New RNA polymerase from *Escherichia coli* infected with bacteriophage T7" Nature. Oct. 17, 1970, vol. 228(5268), pp. 227-231.
Cho, et al. "An unnatural biopolymer" Science 261:1303-5 (1993).

(Continued)

*Primary Examiner* — Jeanine A Goldberg
(74) *Attorney, Agent, or Firm* — Casimir Jones, S.C.

(57) ABSTRACT

The present invention relates to methods and compositions for predicting the risk of obesity. In particular, the present invention provides methods and compositions for determining a subject's risk of obesity based on the presence of polymorphisms in the growth hormone secretagogue receptor (GHSR).

6 Claims, 4 Drawing Sheets

OTHER PUBLICATIONS

Cull, et al. "Screening for receptor ligands using large libraries of peptides linked to the C terminus of the lac repressor" Proc. Natl. Acad. Sci. USA 89: 1865-1869, 1992.

Cummings, et al. "Genetics and pathophysiology of human obesity" Annu Rev Med 54:453-471, 2003.

Cummings, et al. "Ghrelin-leptin tango in body-weight regulation" Gastroenterology, vol. 124 1532-1535, 2003.

Cummings, et al. "Plasma ghrelin levels after diet-induced weight loss or gastric bypass surgery" N Engl J Med. May 23, 2002, vol. 346(21), pp. 1623-1630.

Cwirla, et al. "Peptides on phage: a vast library of peptides for identifying ligands" Proc. Natl. Acad. Sci. 87:6378-6382, 1990.

Devlin, et al. "A comparison of linkage disequilibrium measures for fine-scale mapping" Genomics. Sep. 20, 1995;29 (2):311-22.

Devlin, et al. "Random peptide libraries: a source of specific protein binding molecules" Science 249:404-406 (1990).

Dewitt, et al. ""Diversomers": an approach to nonpeptide, nonoligomeric chemical diversity" Proc. Natl. Acad. Sci. U.S.A. 90:6909-13 (1993).

Erb, et al. "Recursive deconvolution of combinatorial chemical libraries" Proc. Natl. Acad. Sci. USA 91:11422-6 (1994).

Evans, et al. "Establishment in culture of pluripotential cells from mouse embryos" Nature 292:154-6 (1981).

Felici "Selection of antibody ligands from a large library of oligopeptides expressed on a multivalent exposition vector" J. Mol. Biol. 222:301-10 (1991).

Flegal, et al. "Prevalence and trends in obesity among US adults, 1999-2000" JAMA 288:1723-1727 2002.

Fodor, et al. "Multiplexed biochemical assays with biological chips" Nature 364:555-556 (1993).

Frayn, et al. "Insulin resistance, adipose tissue and coronary heart disease" Clin Sci (Lond) 82:1-8 1992.

Gallop, et al. "Applications of combinatorial technologies to drug discovery. 1. Background and peptide combinatorial libraries" J. Med. Chem. 37:1233-51 (1994).

Gossler, et al. "Transgenesis by means of blastocyst-derived embryonic stem cell lines" Proc. Acad. Sci. USA 83:9065-9 (1986).

Hall, et al. "Sensitive detection of DNA polymorphisms by the serial invasive signal amplification reaction" PNAS USA 97:8272 (2000).

Haskell, et al. "Efficient production of transgenic cattle by retroviral infection of early embryos" Mol. Reprod. Dev. vol. 40, pp. 386-390 (1995).

Holst, et al. "Constitutive ghrelin receptor activity as a signaling set-point in appetite regulation" Trends Pharmacol Sci 25: 113-117 2004.

Holst, et al. "High constitutive signaling of the ghrelin receptor—identification of a potent inverse agonist" Mol Endocrinol, vol. 17:2201-2210 2003.

Houghten, et al. "The use of synthetic peptide combinatorial libraries for the identification of bioactive peptides" Biotechniques 13:412-421 (1992).

Jaenisch "Germ line integration and Mendelian transmission of the exogenous Moloney leukemia virus" Proc. Natl. Acad. Sci. USA 73:1260-4 (1976).

Jaenisch "Transgenic animals" Science 240:1468-74 (1988).

Jahner, et al. "De novo methylation and expression of retroviral genomes during mouse embryogenesis" Nature, vol. 298, pp. 623-8 (1982).

Jahner, et al. "Insertion of the bacterial gpt gene into the germ line of mice by retroviral infection" Proc. Natl. Acad Sci. USA 82:6927-31 (1985).

Kacian, et al. "A replicating RNA molecule suitable for a detailed analysis of extracellular evolution and replication" Proc. Natl. Acad. Sci. USA, vol. 69, pp. 3038-3042 (1972).

Keil, et al. "The cardiovascular risk factor profile in the study area Augsburg. Results from the first MONICA survey 1984/85" Acta Med Scand Suppl 728:119-128 1988.

Kim, et al. "Changes in ghrelin and ghrelin receptor expression according to feeding status" Neuroreport. Jul. 18, 2003, vol. 14(10), pp. 1317-1320.

Kissebah, et al. "Quantitative trait loci on chromosomes 3 and 17 influence phenotypes of the metabolic syndrome" Proc Natl Acad Sci USA 97:14478-14483 2000.

Knight "Functional implications of genetic variation in non-coding DNA for disease susceptibility and gene regulation" Clin Sci (Lond) 104:493-501, 2003.

Kojima, et al. "Ghrelin is a growth-hormone-releasing acylated peptide from stomach" Nature 402:656-660, 1999.

Kong, et al. "Synthesis and duplex stability of nucleotides containing cytosine-thymine analogues" Nucleic Acids Res. 1989 17 10373-10383.

Kong, et al. "Synthesis of oligodeoxyribonucleotides containing degenerate bases and their use as primers in the polymerase chain reaction" Nucleic Acids Res. (1992) vol. 20, pp. 5149-5152.

Lam "A new type of synthetic peptide library for identifying ligand-binding activity" Nature 354:82-84 (1991).

Lam "Application of combinatorial library methods in cancer research and drug discovery" Anticancer Drug Des. 12:145-67 (1997).

Luke, et al. "Linkage for BMI at 3q27 region confirmed in an African-American population" Diabetes 52:1284-1287, 2003.

Lyamichev, et al. "Polymorphism identification and quantitative detection of genomic DNA by invasive cleavage of oligonucleotide probes" Nat. Biotech. 17:292-6 (1999).

Marzullo, et al. "The relationship between active ghrelin levels and human obesity involves alterations in resting energy expenditure" J Clin Endocrinol Metab. Feb. 2004;89(2)936-9.

Mattick "RNA regulation: a new genetics?" Nat Rev Genet. Apr. 2004:5(4):316-23.

Nakazato, et al. "A role for ghrelin in the central regulation of feeding" Nature 409, pp. 194-198, 2001.

Needleman, et al. "A general method applicable to the search for similarities in the amino acid sequence of two proteins" J. Mol. Biol. 48, 443-53 (1970).

Noauthors "The World Health Organization MONICA Project (monitoring trends and determinants in cardiovascular disease): a major international collaboration. WHO MONICA Project Principal Investigators" J. Clin. Epidemiol., vol. 41, pp. 105-114 (1988).

Nobrega, et al. "Scanning human gene deserts for long-range enhancers" Science 302:413 (2003).

Pearson, et al. "Improved tools for biological sequence comparison" Proc. Natl. Acad. Sci. (U.S.A.) 85:2444-8 (1988).

Pennacchio, et al. "Genomic strategies to identify mammalian regulatory sequences" Nat Rev Genet. Feb. 2001;2 (2), pp. 100-109.

Petersenn, et al. "Genomic structure and transcriptional regulation of the human growth hormone secretagogue receptor" Endocrinology. Jun. 2001;142(6):2649-59.

Reich, et al. "Quality and completeness of SNP databases" Nat Genet. Apr. 2003;33(4):457-8.

Reynaldo, et al. "The kinetics of oligonucleotide replacements" J. Mol. Biol. 97: 511-520 (2000).

Rice, et al. "A genomewide linkage scan for abdominal subcutaneous and visceral fat in black and white families: The Heritage Family Study" Diabetes 51:848-855 2002.

Robertson, et al. "Germ-line transmission of genes introduced into cultured pluripotential cells by retroviral vector" Nature 323:445-8 (1986).

Sambrook, et al. Molecular Cloning: A Laboratory Manual Cold Spring Harbor Press NY pp. 9.31-9.58 (1989).

Schweitzer, et al. "Aromatic Nonpolar Nucleosides as Hydrophobic Isoteres of Pyrimidine and Purine Nucleosides" J Org. Chem. 1994, vol. 59, pp. 7238-7242.

Schweitzer, et al. "Hydrophobic, Non-Hydrogen-Bonding Bases and Base Pairs in DNA" J. Am. Chem. Soc. 1995 117 1863-1872.

Scott, et al. "Searching for peptide ligands with an epitope library" Science 249:386-390 (1990).

Smith, et al. "Comparison of Biosequences" Adv. Appl. Math. 2: 482 (1981).

Stewart, et al. "Expression of retroviral vectors in transgenic mice obtained by embryo infection" EMBO J. 6:383-8 (1987).

Tschop, et al. "Circulating ghrelin levels are decreased in human obesity" Diabetes. Apr. 2001;50(4):707-9.

TSCOP, et al. "Ghrelin induces adiposity in rodents" Nature 407:908-913, 2000.

Vionnet, et al. "Genomewide search for type 2 diabetes-susceptibility genes in French whites: evidence for a novel suseptibility locus for early-onset diabetes on chromosome 3q27-qte and independent replicaiton of a type 2-diabetes locus on chromosome 1q21-q24" Am J Hum Genet. Dec. 2000, vol. 67-(6), pp. 1470-1480.

Wren, et al. "Ghrelin causes hyperphagia and obesity in rats" Diabetes. Nov. 2001;50(11):2540-7.

Wren, et al. "Ghrelin enhances appetite and increases food intake in humans" J Clin Endocrinol Metab vol. 86, pp. 5992, 2001.

Wu, et al. "A combined analysis of genomewide linkage scans for body mass index from the National Heart, Lung, and Blood Institute Family Blood Pressure Program" Am J Hum Genet, vol. 70, pp. 1247-1256 (2002).

Wu, et al. "The ligation amplification reaction (LAR)—amplification of specific DNA sequences using sequential rounds of template-dependent ligation" Genomics 4:560-9 (1989).

Zhu, et al. "A genome-wide scan for obesity in African-Americans" Diabetes, vol. 51, pp. 541-544, 2002.

Zuckermann, et al. "Discovery of nanomolar ligands for 7-transmembrane G-protein-coupled receptors from a diverse N-(substituted) glycine peptoid library" J. Med. Chem., vol. 37, pp. 2678-2685 (1994).

Wang et al. "Ghrelin receptor gene: identification of several sequence variants in extremely obese children and adolescents." J. of Clinical Endocrinology & Metabolism, 2004 vol. 89, No. I. pp. 157-162.

Baessler et al. "Genetic Linkage and Association of the Growth Hormone Secretagogue Receptor (Ghrelin Receptor) Gene in Human Obesity." Diabetes, 2005 vol. 54, pp. 259-267.

Martin et al. "Lack of association of Ghrelin precursor gene variants and percentage body fat or serum lipid profiles." Obesity, Apr. 2008 vol. 16, No. 4.

Miyasaka et al. "Association of ghrelin receptor gene polymorphism with bulimia nervosa-in Japanese population." J. of Nerual Transmission. 2006 vol. 113, pp. 1279-1285.

Larsen, Lseli. "Genetic aspects of Human obesity." Dan Med Bull, 2006 vol. 53, pp. 224, Abstract only.

* cited by examiner

TABLE 4
Summary of the association of SNPs in the total MONICA Augsburg LVH substudy sample as well as in matched case and control subjects

| SNP | Case subjects | | | | Control subjects | | | | Allele 2 vs. 1 | | | Genotype 22 vs. 11 | | | Genotypes 22 + 12 vs. 11 | | |
|---|---|---|---|---|---|---|---|---|---|---|---|---|---|---|---|---|---|
| | 11 | 12 | 22 | MAF | 11 | 12 | 22 | MAF | OR (95% CI) | P | P(corr) | OR (95% CI) | P | P(corr) | OR (95% CI) | P | P(corr) |
| rs309035 | | | | | | | | | | | | | | | | | |
| Matched | 47 | 59 | 17 | 0.33 | 173 | 103 | 21 | 0.29 | 1.50 (1.10-2.03) | 0.009 | 0.013 | 2.98 (1.46-6.10) | 0.002 | 0.003 | 1.50 (0.99-2.27) | 0.053 | 0.035 |
| Total study | 49 | 65 | 17 | 0.33 | 424 | 275 | 69 | 0.30 | 1.45 (1.11-1.90) | 0.007 | 0.010 | 2.13 (1.16-3.91) | 0.013 | 0.019 | 1.60 (1.10-2.33) | 0.015 | 0.022 |
| rs572169 | | | | | | | | | | | | | | | | | |
| Matched | 50 | 62 | 17 | 0.37 | 182 | 157 | 25 | 0.28 | 1.49 (1.11-2.01) | 0.009 | 0.013 | 2.48 (1.24-4.94) | 0.009 | 0.013 | 1.53 (1.05-2.33) | 0.028 | 0.041 |
| Total study | 52 | 67 | 17 | 0.37 | 451 | 271 | 30 | 0.29 | 1.42 (1.09-1.85) | 0.010 | 0.015 | 1.84 (1.02-3.35) | 0.042 | 0.062 | 1.62 (1.12-2.34) | 0.011 | 0.016 |
| rs518384 | | | | | | | | | | | | | | | | | |
| Matched | 56 | 63 | 15 | 0.34 | 207 | 155 | 16 | 0.25 | 1.59 (1.18-2.16) | 0.003 | 0.004 | 3.47 (1.62-7.44) | 0.0009 | 0.001 | 1.62 (1.09-2.42) | 0.018 | 0.023 |
| Total study | 59 | 65 | 15 | 0.34 | 501 | 301 | 53 | 0.26 | 1.48 (1.13-1.94) | 0.004 | 0.006 | 2.20 (1.17-4.12) | 0.013 | 0.018 | 1.62 (1.13-2.33) | 0.008 | 0.012 |
| rs512092 | | | | | | | | | | | | | | | | | |
| Matched | 57 | 55 | 15 | 0.33 | 200 | 154 | 16 | 0.25 | 1.51 (1.11-2.06) | 0.008 | 0.012 | 3.51 (1.62-7.61) | 0.0009 | 0.001 | 1.45 (0.97-2.16) | 0.070 | 0.103 |
| Total study | 60 | 60 | 15 | 0.33 | 482 | 356 | 50 | 0.26 | 1.41 (1.07-1.80) | 0.014 | 0.021 | 2.15 (1.15-4.04) | 0.015 | 0.022 | 1.40 (1.02-2.11) | 0.040 | 0.059 |
| rs363441 | | | | | | | | | | | | | | | | | |
| Matched | 56 | 58 | 18 | 0.35 | 201 | 149 | 13 | 0.24 | 1.74 (1.28-2.37) | 0.0003 | 0.0004 | 5.04 (2.33-10.9) | 0.00001 | 0.00002 | 1.66 (1.11-2.49) | 0.013 | 0.019 |
| Total study | 59 | 61 | 18 | 0.35 | 493 | 335 | 55 | 0.26 | 1.56 (1.20-2.04) | 0.001 | 0.002 | 2.74 (1.51-5.00) | 0.0007 | 0.001 | 1.61 (1.12-2.31) | 0.009 | 0.013 |

SNPs shown as rs numbers from the dbSNP database. Odds ratios (ORs) with 95% CIs are based on the Armitage best for trend. MAF, minor allele frequency; P(corr), P value corrected for multiple testing.

POLYMORPHIC GHSR NUCLEIC ACIDS AND USES THEREOF

The present application claims priority to U.S. Provisional Application Ser. No. 60/680,087 filed May 12, 2005, which is incorporated herein by reference.

This invention was made with government support under grants R01-DK-54026 and MO1-RR-00058 awarded by the National Institutes of Health. The government has certain rights in the invention.

FIELD OF THE INVENTION

The present invention relates to methods and compositions for predicting the risk of obesity and associated diseases and conditions. In particular, the present invention provides methods and compositions for determining a subject's risk of obesity based on the presence of polymorphisms in the growth hormone secretagogue receptor (GHSR).

BACKGROUND OF THE INVENTION

Obesity and obesity related diseases are a significant health problem. Obesity is an excess proportion of total body fat. A person is considered obese when his or her weight is 20% or more above normal weight. About 39 million Americans currently fall into that category—an all-time high as of 2002. The cost of treating obesity and obesity-related diseases in America accounts for $238 billion, or approximately 20% of the nation's total health care bill, according to the American Obesity Association.

Substantial excess body fat may cause serious health problems. Extra pounds put great strain on the cardiovascular system, contributing to high blood pressure and heart disease, while high fat concentrations can enlarge the liver. Obesity also increases the risk of colorectal cancer.

An additional obesity related illness is adult onset, or Type 2 diabetes. Excessive weight gain may trigger Type 2 diabetes, in which body tissues become resistant to insulin produced by the pancreas. About 80 percent of people with Type 2 diabetes are obese. As a consequence of its microvascular pathology, diabetes is a leading cause of blindness, end-stage renal disease and a variety of debilitating neuropathies. Diabetes is also associated with accelerated atherosclerotic macrovascular disease affecting arteries that supply the heart, brain and lower extremities. As a result, patients with diabetes have a much higher risk of myocardial infarction, stroke and limb amputation.

The exact cause of obesity is still unknown. In addition, the exact causal link between obesity and obesity related illnesses are unknown. Research aimed at determining the cause of obesity and the link with related illnesses has been unsuccessful.

What is needed is a better understanding of the molecular biology and genetics surrounding obesity.

SUMMARY OF THE INVENTION

The present invention relates to methods and compositions for predicting the risk of obesity. In particular, the present invention provides methods and compositions for determining a subject's risk of obesity based on the presence of polymorphisms in the growth hormone secretagogue receptor (GHSR).

Accordingly, in some embodiments, the present invention provides methods and compositions for the determination of a subject's GHSR haplotype or SNP status. In some embodiments, the results are used to determine an individual's susceptibility to obesity or related diseases or conditions (e.g., high blood pressure, heart disease, diabetes, stroke, gall bladder disease, osteoarthritis, sleep apnea, respiratory problems, cancer, dyslipidemia, etc.). The present invention further provides drug-screening methods to screen for compounds that alter the activity of GHSR polypeptides (e.g., polymorphic GHSR polypeptides).

For example, in some embodiments, the present invention provides a method of predicting susceptibility to obesity in a subject, comprising: providing a sample from a subject; and determining the subject's growth hormone secretagogue receptor (GHSR) haplotype to determine the subject's susceptibility to obesity. In some embodiments, a haplotype of rs509035G, rs572169G, rs519384T, rs512692A, rs863441G is correlated with a decreased susceptibility to obesity in the subject. In other embodiments, a haplotype of rs509035A, rs572169A, rs519384A, rs512692T, rs863441C is correlated with a increased susceptibility to obesity in the subject. In some embodiments, the determining the subject's GHSR haplotype comprises a nucleic acid based detection assay (e.g., a sequencing or a hybridization assay). In some embodiments, the subject is not obese.

The present invention further provides a method, comprising: providing a sample from a subject; detecting the genotype of one or more single nucleotide polymorphisms selected from the group consisting of rs509035, rs572169, rs519384, and rs863441; and determining the subject's risk of developing obesity based on the genotype of the single nucleotide polymorphism. In some embodiments, determining the subject's GHSR genotype comprises a nucleic acid based detection assay (e.g., a sequencing Or a hybridization assay). In certain embodiments, the subject is not obese.

The present invention also provides a method, comprising: providing a sample from a subject; and determining the subject's GHSR haplotype; wherein the haplotype is rs509035G, rs572169G, rs519384T, rs512692A, rs863441G or rs509035A, rs572169A, rs519384A, rs512692T, rs863441C.

In yet other embodiments, the present invention provides a kit for determining a subject's risk of developing obesity, comprising: a detection assay, wherein the detection assay is configured to specifically detect the subject's GHSR genotype or haplotype; and instructions for using the detection assay to determining the subject's risk of developing obesity. In some embodiments, the subject's GHSR haplotype is rs509035G, rs572169G, rs519384T, rs512692A, rs863441G or rs509035A, rs572169A, rs519384A, rs512692T, rs863441C. In some embodiments, the detection assay is a nucleic acid based detection assay (e.g., a sequencing or a hybridization assay).

In still further embodiments, the present invention provides a method of screening compounds, comprising: providing a cell comprising a GHSR gene; and one or more test compounds; and contacting the cell with the test compound; and detecting the presence of an altered level of expression of the GHSR gene in the presence of the test compound relative to the level in the absence of the test compound. In some embodiments, the GHSR gene has a haplotype of rs509035G, rs572169G, rs519384T, rs512692A, rs863441G or rs509035A, rs572169A, rs519384A, rs512692T, rs863441C. In some embodiments, the cell is in an animal. In some embodiments, the animal is a non-human mammal. In some embodiments, the non-human mammal is a transgenic non-human mammal, wherein the transgenic non-human mammal comprises a GHSR haplotype of rs509035G, rs572169G, rs519384T, rs512692A, rs863441G or rs509035A, rs572169A, rs519384A, rs512692T, rs863441C. In some embodiments, the animal is obese. In other embodiments, the animal is not obese. In other embodiments, the animal is a human.

DESCRIPTION OF THE FIGURES

FIG. 4 shows Table 4.

DEFINITIONS

Figure 1:
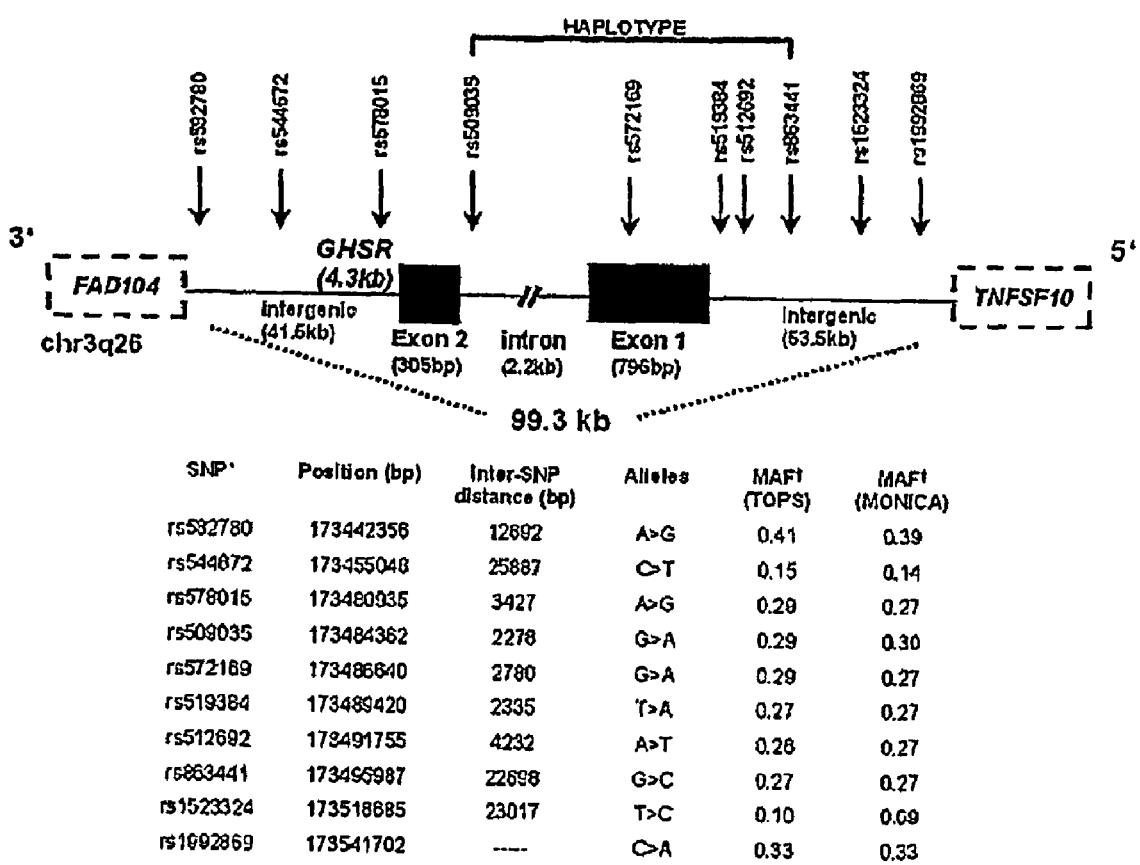
FIG. 1 shows the structure of the GHSR 1a isoform and positions of some of the SNPS analyzed in some embodiments of the present invention.

To facilitate an understanding of the present invention, a number of terms and phrases are defined below:

As used herein, the term "single nucleotide polymorphism" or "SNP", refers to any position along a nucleotide sequence that has one or more variant nucleotides. Single nucleotide polymorphisms (SNPs) are the most common form of DNA sequence variation found in the human genome and are generally defined as a difference from the baseline reference DNA sequence which has been produced as part of the Human Genome Project or as a difference found between a subset of individuals drawn from the population at large. SNPs occur at an average rate of approximately 1 SNP/1000 base pairs when comparing any two randomly chosen human chromosomes. Extremely rare SNPs can be identified which may be restricted to a specific individual or family, or conversely can be found to be extremely common in the general population (present in many unrelated individuals). SNPs can arise due to errors in DNA replication (i.e., spontaneously) or due to mutagenic agents (i.e., from a specific DNA damaging material) and can be transmitted during reproduction of the organism to subsequent generations of individuals.

As used herein, the term "linkage disequilibrium" refers to single nucleotide polymorphisms where the genotypes are correlated between these polymorphisms. Several statistical measures can be used to quantify this relationship (i.e. D', $r^2$, etc) reference (See e.g., Devlin and Risch 1995 Sep. 20; 29(2):311-22). In some embodiments, a SNP-SNP pair is considered to be in linkage disequilibrium if $r^2 > 0.5$, As used herein, the term "haplotype" refers to a group of closely linked alleles that are inherited together.

As used herein, the term "allele" refers to a variant form of a given sequence (e.g., including but not limited to, genes containing one or more SNPs). A large number of genes are present in multiple allelic forms in a population A diploid organism carrying two different alleles of a gene is said to be heterozygous for that gene, whereas a homozygote carries two copies of the same allele.

As used herein, the term "linkage" refers to the proximity of two or more markers (e.g., genes) on a chromosome.

As used herein, the term "allele frequency" refers to the frequency of occurrence of a given allele (e.g., a sequence containing a SNP) in given population (e.g., a specific gender, race, or ethnic group). Certain populations may contain a given allele within a higher percent of its members than other populations. For example, a particular mutation in the breast cancer gene called BRCA1 was found to be present in one percent of the general Jewish population. In comparison, the percentage of people in the general U.S. population that have any mutation in BRCA1 has been estimated to be between 0.1 to 0.6 percent. Two additional mutations, one in the BRCA1 gene and one in another breast cancer gene called BRCA2, have a greater prevalence in the Ashkenazi Jewish population, bringing the overall risk for carrying one of these three mutations to 2.3 percent.

As used herein, the term "in silico analysis" refers to analysis performed using computer processors and computer memory. For example, "in silico SNP analysis" refers to the analysis of SNP data using computer processors and memory.

As used herein, the term "genotype" refers to the actual genetic make-up of an organism (e.g., in terms of the particular alleles carried at a genetic locus). Expression of the genotype gives rise to an organism's physical appearance and characteristics—the "phenotype."

As used herein, the term "locus" refers to the position of a gene or any other characterized sequence on a chromosome.

As used herein the term "disease" or "disease state" refers to a deviation from the condition regarded as normal or average for members of a species, and which is detrimental to an affected individual under conditions that are not inimical to the majority of individuals of that species (e.g., diarrhea, obesity, high blood sugar, nausea, fever, pain, and inflammation etc).

As used herein, the term "treatment" in reference to a medical course of action refer to steps or actions taken with respect to an affected individual as a consequence of a suspected, anticipated, or existing disease state, or wherein there is a risk or suspected risk of a disease state. Treatment may be provided in anticipation of or in response to a disease state or suspicion of a disease state, and may include, but is not limited to preventative, ameliorative, palliative or curative steps. The term "therapy" refers to a particular course of treatment.

The term "gene" (e.g., GHSR gene) refers to a nucleic acid (e.g., DNA) sequence that comprises coding sequences necessary for the production of a polypeptide, RNA (e.g., rRNA, tRNA, etc.), or precursor. The polypeptide, RNA, or precursor can be encoded by a full length coding sequence or by any portion of the coding sequence so long as the desired activity or functional properties (e.g., ligand binding, signal transduction, etc.) of the full-length or fragment are retained. The term also encompasses the coding region of a structural gene, including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments included when a gene is transcribed into heterogeneous nuclear RNA (hnRNA); introns may contain regulatory elements such as enhancers. Introns are removed or "spliced out" from the nuclear or primary transcript; introns therefore are generally absent in the messenger RNA (mRNA) transcript. The mRNA functions during translation to specify the sequence or order of amino acids in a nascent polypeptide. Variations (e.g., mutations, SNPS, insertions, deletions) in transcribed portions of genes are reflected in, and can generally be detected in corresponding portions of the produced RNAs (e.g., hnRNAs, mRNAs, rRNAs, tRNAs).

Where the phrase "amino acid sequence" is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. In this case, the DNA sequence thus codes for the amino acid sequence.

DNA and RNA molecules are said to have "5' ends" and "3'ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5'end" if its 5' phosphate is not linked to the 3' oxygen of a mononucleotide pentose ring and as the "3'end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 µl $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42 C when a probe of about 500 nucleotides in length is employed.

The following terms are used to describe the sequence relationships between two or more polynucleotides: "reference sequence," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

As applied to polynucleotides, the term "substantial identity" denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a splice variant of the full-length sequences.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method.

As used herein, the term "probe" or "hybridization probe" refers to an oligonucleotide (i.e., a sequence of nucleotides), whether occurring naturally as in a purified restriction digest or produced synthetically, recombinantly or by PCR amplification, that is capable of hybridizing, at least in part, to another oligonucleotide of interest. A probe may be single-stranded or double-stranded. Probes are useful in the detection, identification and isolation of particular sequences. In some preferred embodiments, probes used in the present invention will be labeled with a "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target" refers to a nucleic acid sequence or structure to be detected or characterized.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include comprise modified forms of deoxyribonucleotides as well as ribonucleotides.

As used herein, the term "recombinant DNA molecule" as used herein refers to a DNA molecule that is comprised of segments of DNA joined together by means of molecular biological techniques.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acids encoding a polypeptide include, by way of example, such nucleic acid in cells ordinarily expressing the polypeptide where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (e.g., 10 nucleotides, 11, . . . , 20, . . . ).

As used herein, the term "purified" or "to purify" refers to the removal of contaminants from a sample. As used herein, the term "purified" refers to molecules (e.g., nucleic or amino acid sequences) that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of labeled antibodies.

The term "test compound" refers to any chemical entity, pharmaceutical, drug, and the like that are tested in an assay (e.g., a drug screening assay) for any desired activity (e.g., including but not limited to, the ability to treat or prevent a disease, illness, sickness, or disorder of bodily function, or otherwise alter the physiological or cellular status of a sample). Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "label" as used herein refers to any atom or molecule that can be used to provide a detectable (preferably quantifiable) effect, and that can be attached to a nucleic acid or protein. Labels include but are not limited to dyes; radiolabels such as $^{32}$P; binding moieties such as biotin; haptens such as digoxygenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

The term "signal" as used herein refers to any detectable effect, such as would be caused or provided by a label or an assay reaction.

As used herein, the term "detector" refers to a system or component of a system, e.g., an instrument (e.g. a camera, fluorimeter, charge-coupled device, scintillation counter, etc) or a reactive medium (X-ray or camera film, pH indicator, etc.), that can convey to a user or to another component of a system (e.g., a computer or controller) the presence of a signal or effect. A detector can be a photometric or spectrophotometric system, which can detect ultraviolet, visible or infrared light, including fluorescence or chemiluminescence; a radiation detection system; a spectroscopic system such as nuclear magnetic resonance spectroscopy, mass spectrometry or surface enhanced Raman spectrometry; a system such as gel or capillary electrophoresis or gel exclusion chromatography; or other detection system known in the art, or combinations thereof.

The term "detection" as used herein refers to quantitatively or qualitatively identifying an analyte (e.g., DNA, RNA or a protein) within a sample. The term "detection assay" as used herein refers to a kit, test, or procedure performed for the purpose of detecting an analyte nucleic acid within a sample. Detection assays produce a detectable signal or effect when performed in the presence of the target analyte, and include but are not limited to assays incorporating the processes of hybridization, nucleic acid cleavage (e.g., exo- or endonuclease), nucleic acid amplification, nucleotide sequencing, primer extension, or nucleic acid ligation.

The terms "assay data" and "test result data" as used herein refer to data collected from performance of an assay (e.g., to detect or quantitate a gene, SNP or an RNA). Test result data may be in any form, i.e., it may be raw assay data or analyzed assay data (e.g., previously analyzed by a different process). Collected data that has not been further processed or analyzed is referred to herein as "raw" assay data (e.g., a number corresponding to a measurement of signal, such as a fluorescence signal from a spot on a chip or a reaction vessel, or a number corresponding to measurement of a peak, such as peak height or area, as from, for example, a mass spectrometer, HPLC or capillary separation device), while assay data that has been processed through a further step or analysis (e.g., normalized, compared, or otherwise processed by a calculation) is referred to as "analyzed assay data" or "output assay data".

As used herein, the term "database" refers to collections of information (e.g., data) arranged for ease of retrieval, for example, stored in a computer memory. A "genomic information database" is a database comprising genomic information, including, but not limited to, polymorphism information (i.e., information pertaining to genetic polymorphisms), genome information (i.e., genomic information), linkage information (i.e., information pertaining to the physical location of a nucleic acid sequence with respect to another nucleic acid sequence, e.g., in a chromosome), and disease association information (i.e., information correlating the presence of or susceptibility to a disease to a physical trait of a subject, e.g., an allele of a subject). "Database information" refers to information to be sent to a databases, stored in a database, processed in a database, or retrieved from a database. "Sequence database information" refers to database information pertaining to nucleic acid sequences. As used herein, the term "distinct sequence databases" refers to two or more databases that contain different information than one another. For example, the dbSNP and GenBank databases are distinct sequence databases because each contains information not found in the other.

As used herein the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "communication network" refers to any network that allows information to be transmitted from one location to another. For example, a communication network for the transfer of information from one computer to another includes any public or private network that transfers information using electrical, optical, satellite transmission, and the like. Two or more devices that are part of a communication network such that they can directly or indirectly transmit information from one to the other are considered to be "in electronic communication" with one another. A computer network containing multiple computers may have a central computer ("central node") that processes information to one or more sub-computers that carry out specific tasks ("sub-nodes"). Some networks comprises computers that are in "different geographic locations" from one another, meaning that the computers are located in different physical locations (i.e., aren't physically the same computer, e.g., are located in different countries, states, cities, rooms, etc.).

As used herein, the term "detection assay component" refers to a component of a system capable of performing a detection assay. Detection assay components include, but are not limited to, hybridization probes, buffers, and the like.

As used herein, the term "a detection assays configured for target detection" refers to a collection of assay components that are capable of producing a detectable signal when carried out using the target nucleic acid. For example, a detection assay that has empirically been demonstrated to detect a particular single nucleotide polymorphism is considered a detection assay configured for target detection.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes)

containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

DETAILED DESCRIPTION OF THE INVENTION

Obesity is a common multifactorial disorder of considerable heterogeneity and, as a pivotal component of the metabolic syndrome, a major risk factor for type 2 diabetes, hypertension, and coronary heart disease as well as premature cardiovascular morbidity and death (Frayn et al., Clin Sci (Lond) 82:1-8, 1992). Together with its associated pathologic features, obesity is among the major causes of illness and death worldwide, as its prevalence continues to rise dramatically (Flegal et al., 1999-2000. JAMA 288:1723-1727, 2002).

The etiology of obesity is complex, determined by the interplay of genetic and environmental factors. Epidemiological studies have demonstrated a substantial heritable component to the risk for obesity; specifically, 50-70% of the variation in BMI may be attributable to genetic factors (Allison et al., Int J Obes Relat Metab Disord 20:501-506, 1996).

Experiments conducted during the course of development of the present invention performed a genomewide linkage scan on a large cohort of Caucasian families from which chromosome 3q26-q29 was localized a major quantitative trait locus (QTL) strongly linked to six phenotypes of obesity and the metabolic syndrome (Kissebah et al., Proc Natl Acad Sci USA 97:14478-14483, 2000). This QTL has been replicated in several studies and represents one of the most stable findings in complex human genetics (Vionnet et al., Am J Hum Genet. 67:1470-1480, 2000; Rice et al., Diabetes 51:848-855, 2002; Wu et al., Am J Hum Genet. 70:1247-1256, 2002; Zhu et al., Diabetes 51:541-544, 2002; Luke et al., Diabetes 52:12841287, 2003).

A comprehensive review of the available genomic information in the QTL region revealed a positional candidate gene of 4.3 kb in length encoding the growth hormone secretagogue, or ghrelin, receptor (GHSR). GHSR is known to be involved in growth hormone secretion (Kojima et al., Nature 402:656-660, 1999; Petersenn et al., Endocrinology 142:2649-2659, 2001). Its major physiological role, however, appears to be in regulating food intake and energy homeostasis by partaking in neuronal mechanisms involving neuropeptide Y and agouti-related protein (Tschop et al., Nature 407:908-913, 2000; Nakazato et al., Nature 409:194-198, 2001; Cummings et al., Annu Rev Med 54:453-471, 2003; Holst et al., Mol Endocrinol 17:2201-2210, 2003). The endogenous GHSR ligand, ghrelin, plays a key role as the major orexigenic hormone. It is secreted in the gastrointestinal tract and is carried to the hypothalamic areas that govern food intake, thereby counterbalancing the effects of a multitude of anorectic hormones, such as leptin, insulin, and PYY3-36 (Holst et al., Trends Pharmacol Sci 25:113-117, 2004).

The importance of ghrelin in the central regulation of feeding has been demonstrated in animals and humans (Wren et al., J Clin Endocrinol Metab 86: 5992, 2001; Wren et al., Diabetes 50:2540-2547, 2001). Ghrelin administration increases appetite and food intake in normal subjects and patients with decreased appetite, such as those suffering from cancer cachexia (Wren et al., J Clin Endocrinol Metab 86: 5992, 2001). It reduces insulin secretion and enhances energy intake by 30% (Broglio et al., J Clin Endocrinol Metab 86:5083-5086, 2001). Moreover, given that plasma ghrelin levels have been shown to be lower in obese subjects (Tschop et al., Diabetes 50:707-709, 2001; Cummings et al., N Engl J Med 346:1623-1630, 2002), recent evidence suggests that obesity is associated with an impairment of the entire ghrelin system Marzullo et al., J Clin Endocrinol Metab 89:936-939, 2004).

A family-based linkage disequilibrium (LD) study was performed in 178 pedigrees as well as in an independent case-control study from the general population. The LD and haplotype structure of the genomic region encompassing the GHSR gene was investigated and the role of common sequence variants and haplotypes in obesity were analyzed. Linkage and association of five single nucleotide polymorphisms (SNPs) and the two most common five-marker haplotypes with obesity was observed in the family cohort. In addition, an association of the same SNPs and haplotypes with obesity and the quantitative phenotype BMI was observed in the general population. The present invention is not limited to a particular mechanism. Indeed, an understanding of the mechanism is not necessary to practice the present invention. Nonetheless, it is contemplated that the replication of the findings, together with the location and biological function of the GHSR gene, indicate that this gene region is involved in the pathogenesis of the complex disease of obesity.

Experiments conducted during the course of development of the present invention investigated the relation between common sequence variants and haplotypes covering the GHSR gene region with obesity phenotypes in families and in an independent sample of the general population. The present study offers the first comprehensive analysis of LD, genetic variants, and haplotype structure across the entire GHSR gene region in two independent cohorts: families and the general population. The initial LD analysis in the 99.3-kb region revealed an LD block consisting of five SNPs in the GHSR gene region, which compared very well in both study cohorts. Subsequent experiments focused on these five SNPs and the five-SNP haplotypes. Linkage between all five SNPs and BMI was observed, as well as evidence for transmission disequilibrium for the minor alleles of the SNPs as well as for the two most common five-SNP haplotypes with the obesity affection status. The replication of these findings in an independent sample of the general population further supports an association of GHSR gene variants with human obesity. Haplotypes or one in LD with them account in part for the observed linkage signal. Thus, the results of experiments conducted during the course of development of the present invention implicate common haplotypes in this gene region in the pathogenesis of human obesity.

The extent of the high-LD region was analyzed by covering the entire gene region, including the surrounding genomic regions close to the neighboring genes, with SNPs. The identified high-LD region encompasses part of the intron, exon 1, and the 5' adjacent region extending 8.8 kb past the 5' end of the gene, but not the flanking genes. Therefore, it is unlikely that the association between variants of the GHSR gene and obesity is seen because of LD with the proper causal mutation in one of the neighboring genes. In addition, SNPs that were not included in the high-LD block were analyzed for association and none of the SNPs showed evidence for association with the obesity affection status or BMI. This indicates that genetic variations within the LD block encompassing the GHSR gene, and not within neighboring genes, are related to obesity phenotypes.

Further experiments conducted during the course of development of the present invention focused only on common sequence variants, as it is more likely that these variants play a role in the general population. SNPs located in noncoding and intergenic regions were included, rather than exclusively focusing on the coding region. This encompassed variants leading to altered gene expression (Knight et al., Clin Sci (Lond) 104:493-501, 2003). Gene regulation is the result of the combinatorial action of multiple transcription factors binding at multiple sites in and near a gene and therefore can be affected by multiple SNPs. Gene regulatory elements reside in noncoding and intergenic regions (Pennacchio et al., Nat Rev Genet. 2:100-109, 2001; Mattick, Nat Rev Genet. 5:316-323, 2004). These enhancers are able to modulate gene expression over long distances, turning intergenic regions into reservoirs for sequence elements containing important functions (Nobrega et al., Science 302:413, 2003). Little is known about the impact of sequence variations in these regions. In experiments conducted during the course of development of the present invention, SNPs located in the intergenic region past the 5' end of the GHSR gene showed stronger association than the SNPs located in the coding or intronic region of the gene. The present invention is not limited to a particular mechanism. Indeed, an understanding of the mechanism is not necessary to practice the present invention. Nonetheless, it is contemplated that these data suggest that the promoter, regulatory elements or transcriptional initiation are involved.

The associated minor allele haplotype (haplotype 2) confers susceptibility to obesity. The major allele haplotype (haplotype 1) acts in a reverse fashion by lowering the risk of obesity. Either effect is present independent of carrying one or two copies. The effect is strongest in those presenting with two copies of the respective haplotype and decreases with the number of copies.

The ghrelin receptor, encoded by the GHSR gene, along with its endogenous ligand ghrelin, provides the only hormonal, appetite-stimulatory input that counterbalances a large number of inhibitory signals that are mediated by leptin, insulin, and PYY3-36 (Cummings et al., Annu Rev Med 54:453-471, 2003; Cummings et al., Gastroenterology 124: 1532-1535, 2003; Barazzoni et al., Gastroenterology 124: 1188-1192, 2003). GHSR is expressed in neuropeptide Y— and agouti-related protein-containing neurons in the hypothalamus that respond to ghrelin by increasing their firing rate (Holst et al., Trends Pharmacol Sci 25:113-117, 2004). Recently, it was shown that during fasting, GHSR expression is increased eightfold, which would be expected to result in an increase in receptor signaling and thereby an increase in appetite (Kim et al., Neuroreport 14:1317-1320, 2003). Accordingly, it is contemplated that genetic variations in the ghrelin receptor gene, and thereby altered expression of the receptor protein, result in altered signaling and consequently altered regulation of appetite. Thus, increased ghrelin receptor expression is expected to be associated with obesity. It was recently shown that the ghrelin receptor exhibits a high constitutive activity signal of 50% efficacy between meals and thus provides a set point for food intake between meals (Holst et al., Mol Endocrinol 17:2201-2210, 2003). The present invention is not limited to a particular mechanism. Indeed, an understanding of the mechanism is not necessary to practice the present invention. Nonetheless, it is contemplated that an increase in this constitutive activity based on genetic variation, such as the "susceptible" haplotype 2, results in decreased sensitivity to the multiple inhibitory signals and consequently promotes snack-eating behavior between meals. It is further contemplated that drugs blocking this constitutive activity of the ghrelin receptor reduces the craving for desserts and intermeal snacks by increasing sensitivity to inhibitory signals (Holst et al. Trends Pharmacol Sci 25:113-117, 2004).

Thus, it is contemplated that genetic variations in the ghrelin receptor gene change either ghrelin receptor expression or receptor properties and thereby have an effect on appetite regulation by altered signaling, altered response to ghrelin, or an impaired capability to counterbalance inhibitory signals. A greater susceptibility to obesity is a consequence.

Accordingly, in some embodiments, the present invention provides methods and compositions for the determination of a subject's GHSR haplotype or SNP status. In some embodiments, the results are used to determine an individual's susceptibility to obesity or to particular obesity therapies, treatment, or interventions. The present invention further provides drug-screening methods to screen for compounds that alter the activity of GHSR polypeptides (e.g., polymorphic GHSR polypeptides).

I. Detection Assays

The present invention provides comprehensive systems and methods for the characterization of GHSR genotypes. For example, the present invention provides systems and methods of characterizing both the identity of polymorphisms in and around the GHSR gene, as well as copy number of either or both the GHSR gene and genic regions or portions thereof to characterize individuals as having a particular GHSR genotype.

In some preferred embodiments, detection assays are configured to analyze multiple GHSR SNPs in a single assay (e.g., Multiplex assay). Exemplary detection assays are described below. It is contemplated that the below described detection assays can be configured for multiplex detection.

There are a wide variety of detection technologies available for determining the sequence of a target nucleic acid at one or more locations. For example, there are numerous technologies available for detecting the presence or absence of SNPs. Many of these techniques require the use of an oligonucleotide to hybridize to the target. Depending on the assay used, the oligonucleotide is then cleaved, elongated, ligated, disassociated, or otherwise altered, wherein its behavior in the assay is monitored as a means for characterizing the sequence of the target nucleic acid.

A. INVADER Assay

While the systems and methods of the present invention are not limited to any particular detection assay, the following description illustrates the invention when used in conjunction with the INVADER assay (Third Wave Technologies, Madison Wis.; See e.g., U.S. Pat. Nos. 5,846,717, 5,985,557, 5,994,069, and 6,001,567 and PCT Publications WO 97/27214 and WO 98/42873, Lyamichev et al., Nat. Biotech., 17:292 (1999), Hall et al., PNAS, USA, 97:8272 (2000), U.S. Patent Applications 20040014067, 20030152971, 20030152942, 20030143585, 20040018489, 20030082544, and 20020119454, each of which incorporated herein by reference in their entireties) to detect a SNP. The INVADER assay provides ease-of-use and sensitivity levels that, when used in conjunction with the systems and methods of the present invention, find use in detection panels, ASRs, and clinical diagnostics. One skilled in the art will appreciate that specific and general features of this illustrative example are generally applicable to other detection assays.

The INVADER assay provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced.

The INVADER assay provides detections assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, (Reynaldo, et al., J. Mol. Biol. 97: 511-520 [2000]), multiple probes can hybridize to the same target, allowing multiple cleavages, and the generation of multiple cleavage products.

B. Direct sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

C. PCR Assay

In some embodiments of the present invention, variant sequences are detected using a PCR-based assay. In some embodiments, the PCR assay comprises the use of oligonucleotide primers that hybridize only to the variant or wild type allele (e.g., to the region of polymorphism or mutation). Both sets of primers are used to amplify a sample of DNA. If only the mutant primers result in a PCR product, then the patient has the mutant allele. If only the wild-type primers result in a PCR product, then the patient has the wild type allele.

D. Fragment Length Polymorphism Assays

In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

i. RFLP Assay

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are generally separated by gel electrophoresis and may be visualized by ethidium bromide staining. The length of the fragments is compared to molecular weight markers and fragments generated from wild-type and mutant controls.

ii. CFLP Assay

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. In preferred embodiments, one or both strands are labeled. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by denaturing gel electrophoresis) and visualized (e.g., by autoradiography, fluorescence imaging or staining). The length of the fragments is compared to molecular weight markers and fragments generated from wild-type and mutant controls.

E. Hybridization Assays

In some embodiments of the present invention, variant sequences are detected a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

i. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

ii. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

iii. Enzymatic Detection of Hybridization

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of DNA polymerases such as AMPLITAQ DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

II. Data Analysis

In some embodiments, a computer-based analysis program is used to translate the raw data generated by the detection assay (e.g., the genotype of a GHSR gene) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., GHSR haplotype), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of developing obesity or related complications) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

III. Kits

In some embodiments, the present invention provides kits for the detection of GHSR polymorphisms. In some embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results. In some embodiments, individual probes and reagents for detection of GHSR polymorphisms are provided as analyte specific reagents. In other embodiments, the kits are provided as in vitro diagnostics.

IV. Drug Screening

In some embodiments, the present invention provides drug screening assays (e.g., to screen for anti-obesity drugs, appetite suppression drugs, etc.). In some embodiments, the screening methods of the present invention utilize polymorphic forms of GHSR. For example, in some embodiments, the present invention provides methods of screening for compounds that alter (e.g., decrease) the activity of one or more polymorphic forms of GHSR. In other embodiments, the drug screening methods described below are used to screen compounds known for use in treating obesity with different polymorphic forms of GHSR.

In one screening method, candidate compounds are evaluated for their ability to alter (e.g., increase or decrease) GHSR expression by contacting a compound with a cell expressing GHSR and then assaying for the effect of the candidate compounds on expression. In some embodiments, the effect of candidate compounds on expression of GHSR is assayed for by detecting the level of GHSR mRNA expressed by the cell. mRNA expression can be detected by any suitable method, including but not limited to, those disclosed herein.

In other embodiments, the effect of candidate compounds is assayed by measuring the level of GHSR polypeptide. The level of polypeptide expressed can be measured using any suitable method, including but not limited to, those disclosed herein or by monitoring a phenotype (e.g., body mass).

In some embodiments, in vitro drug screens are performed using purified wild type or dominant active GHSR and binding partners or signaling partners thereof. Compounds are screened for their ability to interact with GHSR proteins and inhibit or enhance GHSR function or the interaction of GHSR with binding partners (e.g., ghrelin).

In still further embodiments, cells or transgenic animals having altered (e.g., polymorphic) GHSR genes are utilized in drug screening applications. For example, in some embodiments, compounds are screened for their ability appetite or body mass in GHSR mice with a particular polymorphic form of GHSR.

In yet other embodiments, subjects (e.g., human subject) are enrolled in clinical trials to test dosages of anti-obesity or other related drugs (e.g., new drugs). In preferred embodiments, subjects having polymorphic GHSR are included in clinical trials to test anti-obesity drugs.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

IV. Transgenic Animals Expressing GHSR Polymorphic Sequences

The present invention contemplates the generation of transgenic animals comprising an exogenous GHSR gene or mutants and variants thereof (e.g., single nucleotide polymorphisms). In preferred embodiments, the transgenic animal displays an altered phenotype (e.g., altered body mass) as compared to wild-type animals. Methods for analyzing the presence or absence of such phenotypes include but are not limited to, those disclosed herein.

The transgenic animals or natural variants having equivalent genotypes of the present invention find use in drug (e.g., anti-obesity) screens. In some embodiments, test compounds (e.g., a drug that is suspected of being useful as an anti-obesity) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Stewart, et al, EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized knock-out gene function or create deletion mutants (e.g., truncation mutants). Methods for homologous recombination are described in U.S. Pat. No. 5,614,396, incorporated herein by reference.

Experimental

The following example is provided in order to demonstrate and further illustrate certain preferred embodiments and aspects of the present invention and are not to be construed as limiting the scope thereof.

EXAMPLE 1

GHSR Polymorphisms

This Example describes the association of SNPs in the GHSR gene with obesity.

A. Methods

The family subjects of the study, a large group of Caucasian families consisting of obese and nonobese members residing in the midwestern U.S., were ascertained through the TOPS (Take Off Pounds Sensibly) Club membership as part of the Metabolic Risk and Complications of Obesity Genes project at the Medical College of Wisconsin. The ascertainment strategies and exclusion criteria have been previously published (Kissebah et al., supra). Informed consent was obtained from all participants. Data were based on results obtained from 1,302 phenotyped individuals distributed among 178 families (average 7.3 members per family; 441 founders; both parents available for genotyping in 148 families; average generations 2.3). These families have been identified as primary contributors to the QTL on chromosome 3. In all, 1,095 DNA samples were available for genotyping in the present study, including samples of 307 (28%) men and 788 (72%) women. Research protocols were approved by the institutional review board of the Medical College of Wisconsin.

For the general population arm of the study, data from subjects in the Monitoring Trends and Determinants in Cardiovascular Disease (MONICA) Augsburg left ventricular hypertrophy (LVH) substudy, as part of the Third MONICA Augsburg survey, which now is continued in the framework of KORA (Cooperative Health Research in the Augsburg Area) were used. The study population of the LVH substudy was sampled from the general population of the city of Augsburg, Germany, in 1994/1995, which originated from a sex- and age-stratified cluster sample of all German residents of the city of Augsburg. The Augsburg project was part of the international collaborative World Health Organization MONICA study (WHO MONICA Project Principal Investigators: The World Health Organization MONICA Project J Clin Epidemiol 41:105-114, 1988). The study design, sampling frame, and data collection methods have been described in detail elsewhere (Keil et al., Acta Med Scand Suppl 728:119-128, 1988). All the participants gave written informed consent. The LVH substudy represents individuals aged 25-74 years, with 300 subjects for each 10-year increment (n=1,674) (Keil et al., supra). Of these, 1,418 DNA samples were available for genotyping in the present study, including 724 men (51%) and 694 women (49%). The study was approved by the local ethics committee.

BMI was calculated as weight (kg) divided by height (m) squared. In both cohorts, obesity was defined by a BMI>32 $kg/m^2$. Subjects were classified as "unaffected" if they presented with a BMI<28 $kg/m^2$. These cutoff values were chosen to ensure clear phenotypes and avoid misclassification regarding affection status. The obesity affection status of subjects with a BMI of 28-32 $kg/m^2$ was treated as "unknown."

SNPs and Genotyping Methods

To obtain complete coverage of the GHSR gene, 10 SNPs covering the GHSR gene and its flanking regions were selected from the SNP public databases (dbSNP; available at the Internet site of NCBI.) (FIG. 1). Validated SNPs with a minor allele frequency of >5% were preferred. Priority was given to SNPs submitted multiple times than to SNPs discovered by The SNP Consortium (Reich et al., Nat Genet. 33:457-458, 2003; Carlson et al., Nat Genet. 33:518-521, 2003). Regarding the intergenic regions, SNPs located in highly conserved noncoding regions were preferred. Of the 10 selected SNPs, 1 was located in exon 1, 1 was in the intron, 3 were within 41.5 kb past the 3' end of the gene, and 5 covered a region of 53.5 kb past the 5' end of the gene. The coding SNP (rs572169) led to a synonymous amino acid substitution. The eight SNPs located beyond the boundaries of the gene were picked to determine the extent of LD and explore the impact of sequence variations in noncoding and intergenic regions on the disease. In total, a 99.3-kb region was covered with SNPs, with an average resolution of one SNP per 10 kb.

B. Results

Phenotypic Characteristics

The phenotypic characteristics of TOPS families and the MONICA LVH population are presented in Table 1. In TOPS families, the mean BMI and prevalence of obesity in men and women were markedly different (P<0.001). In the MONICA LVH population, the prevalence of obesity was significantly higher in women than in men (P<0.001).

TABLE 1

|  | Men | Women |
|---|---|---|
| TOPS | | |
| n | 307 | 788 |
| Age (years) | 50.9 ± 17.6 | 46.0 ± 14.4 |
| obesity affection status (%) | 24.7 | 50.1 |
| BMI ($kg/m^2$) | | |
| Total sample | 29.1 ± 5.6 | 33.1 ± 8.4 |
| Affected | 37.0 ± 4.5 (75) | 39.8 ± 6.2 (393) |
| Unaffected | 24.5 ± 2.4 (141) | 24.3 ± 2.4 (244) |
| Body weight (kg) | 93.2 ± 21.1 | 89.7 ± 24.2 |
| Waist-to-hip ratio | 0.95 ± 0.09 | 0.85 ± 0.10 |
| Hypertension (%) | 41.8 | 36.0 |
| Type 2 diabetes (%) | 7.9 | 7.8 |
| Current smoker (%) | 37.2 | 31.0 |
| MONICA | | |
| n | 724 | 694 |
| Age (years) | 52.5 ± 13.9 | 51.6 ± 13.6 |
| Obesity affection status (%) | 9.9 | 16.1 |
| BMI ($kg/m^2$) | | |
| Total sample | 27.0 ± 3.5 | 26.4 ± 4.7 |
| Affected | 34.6 ± 2.5 (50) | 35.0 ± 2.7 (89) |
| Unaffected | 24.9 ± 2.1 (457) | 23.8 ± 2.5 (463) |

TABLE 1-continued

| | Men | Women |
|---|---|---|
| Body weight (kg) | 81.9 ± 11.5 | 68.8 ± 11.9 |
| waist-to-hip ratio | 0.92 ± 0.06 | 0.80 ± 0.06 |
| Hypertension (%) | 41.9 | 33.4 |
| Type 2 diabetes (%) | 5.2 | 3.0 |
| Current smoker (%) | 30.2 | 23.6 |

Data are means ± SD, with (n) where appropriate, unless otherwise indicated. The obesity affection status is defined as a BMI >32 kg/m². Hypertension is defined as systolic blood pressure >140 mmHg, diastolic blood pressure >90 mmHg, or a history of hypertension. Because of nonindependent observations in TOPS families, characteristics are descriptive. Subjects classified as "unknown" are not shown.

Figure 2:
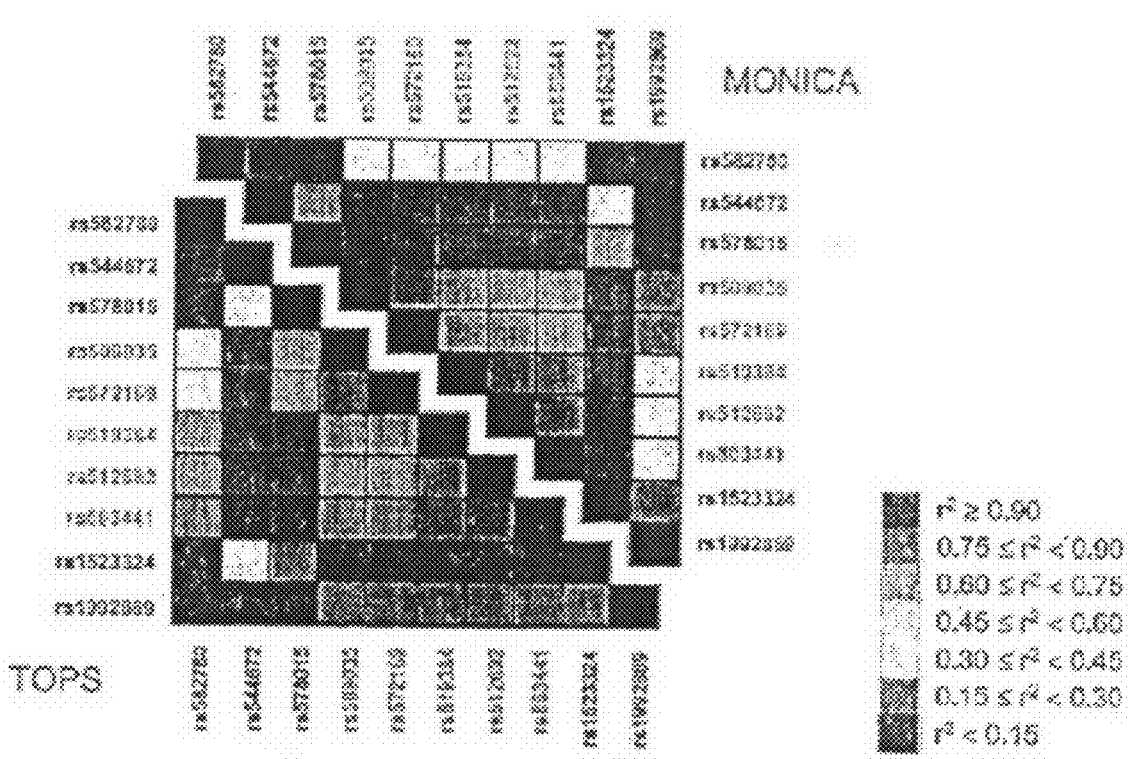
FIG. 2 shows the patter of pairwise linkage disequilibrium between SNPS in the GHSR gene.

Linkage Disequilibrium Evaluation and Haplotype Structure in Families and the General Population FIG. 1 depicts the gene structure and all SNPs used in this study, including their position and general characteristics based on the July 2003 release of the Golden Path Genome Browser. The pairwise LD block structure defined by the 10 SNPs covering a 99.3-kb region in TOPS families and the MONICA LVH population is shown in FIG. 2. A region of strong LD ($r2>0.75$) was detected between five SNPs (rs509035, rs572169, rs519384, rs512692, and rs863441), and the LD pattern was comparable in both study populations. The pairwise LD between these five SNPs spanned a 11.63-kb region and encompassed most of the intron, exon 1, and 5' adjacent region of the GHSR gene.

According to this high-LD block, five-marker haplotypes were constructed. Only 3 of 25 possible haplotypes were estimated to have frequencies >0.01 in obese and/or nonobese subjects. Less frequently occurring haplotypes were not shown, owing to concern over the accuracy of low-frequency alleles in the expectation-maximization algorithm. The two most frequently occurring haplotypes, haplotypes 1 and 2, comprised 94% of total chromosomes in subjects of both study cohorts (Tables 2 and 3). For further linkage and association analyses, studies focused on those markers that contributed to this haplotype block. The relationship between these five SNPs and/or five-marker haplotypes and obesity phenotypes was analyzed. To ensure that the SNPs that were not included in the high-LD block were not associated with obesity, association analysis was performed for these SNPs. None of the SNPs showed any evidence for association with the obesity affection status or with BMI.

TABLE 2

TDT of association with obesity-affection status in 148 trios selected from the TOPS families and family-based association test using FBAT analysis

| | | | Trio TDT (n probands with allele) | | | |
|---|---|---|---|---|---|---|
| SNP/haplotype | Frequency | Allele | Transmitted | Not transmitted | P | FBAT P |
| rs509035 | 0.71 | G | 24 | 37 | 0.096 (0.137) | 0.021 (0.030) |
| | 0.29 | A | 37 | 24 | | |
| rs572169 | 0.71 | G | 23 | 38 | 0.055 (0.079) | 0.032 (0.046) |
| | 0.29 | A | 38 | 23 | | |
| rs519384 | 0.73 | T | 23 | 37 | 0.070 (0.100) | 0.010 (0.014) |
| | 0.27 | A | 37 | 23 | | |
| rs512692 | 0.74 | A | 21 | 38 | 0.027 (0.039) | 0.033 (0.047) |
| | 0.26 | T | 38 | 21 | | |
| rs863441 | 0.73 | G | 22 | 37 | 0.051 (0.073) | 0.012 (0.017) |
| | 0.27 | C | 37 | 22 | — | — |
| Haplotype 1 | 0.69 | G-G-T-A-G | — | — | — | 0.025 (NA) |
| Haplotype 2 | 0.25 | A-A-A-T-C | — | — | — | 0.045 (NA) |
| Haplotype 3 | 0.03 | A-A-T-A-G | — | — | — | 0.905 (NA) |

SNPs are shown as rs numbers from the dbSNP database, Haplotypes are derived from the five SNPs contributing to the high-LD block ($r^2 > 0.75$). P values were corrected for multiple testing (shown in parentheses). P values for trio TDT are based on the TDT statistic; P values for FBAT are based on the FBAT (-o option) statistic, NA, correction not applied.

TABLE 3

Haplotype structures of the LD block with their frequencies and association with obesity in the general population (MONICA Augsburg LVH substudy)

| | Haplotypes | | | | | Frequency | | | |
|---|---|---|---|---|---|---|---|---|---|
| ID | rs609035 | rs573169 | rs619384 | rs512692 | rs863441 | Obese | Non-obese | Asymptotic P | Empirical P |
| 1 | G | G | T | A | G | 0.61 | 0.69 | 0.002 | 0.002 |
| 2 | A | A | A | T | C | 0.33 | 0.35 | 0.002 | 0.001 |
| 3 | A | A | T | A | G | 0.04 | 0.04 | 0.474 | 0.452 |

Haplotypes are derived from the five SNPs contributing to the high-LD block ($r^2 > 0.75$). Asymptotic P values are based on haplotype trend regression analysis; empirical P values are based on 50,000 permutations. The permutation test was implemented in the haplotype trend regression analysis program.

Family Data: Genetic Linkage and Transmission Disequilibrium of Snps and Haplotypes in the GHSR Region.

To test for linkage in families, the variance component methodology was used. Evidence for linkage with the quantitative phenotype BMI was detected for all five SNPs forming the high-LD block depicted in FIG. 2 ($P<0.05$). Thus, the SNP genotype data confirmed linkage to the previously shown QTL on chromosome 3q (Kissebah et al., supra).

To test for transmission disequilibrium in families, both the conventional TDT statistic (in the 148 trios with one randomly selected affected offspring) and the FBAT statistic (considering all family members) were applied for each of the SNPs contributing to the haplotype. The TDT analysis revealed increased transmission for the minor alleles of the five SNPs to obese offspring (Table 2). A slightly stronger pattern of association of the single SNPs with the obesity-affection status was observed when the FBAT statistic was used ($P<0.05$ for all five SNPs) (Table 2).

In addition, transmission disequilibrium for the two most frequent haplotypes, one consisting of the five major alleles (haplotype 1) and the other consisting of the five minor alleles (haplotype 2) was observed (Table 2). Corresponding to the "susceptible" haplotype, haplotype 2 had a greater number of transmissions to affected offspring ($P=0.025$). In contrast, the transmission rate of haplotype 1 was significantly reduced in these offspring, suggesting that this haplotype is "nonsusceptible" or resistant to obesity ($P=0.045$).

After reconstructing the individual haplotypes, evidence for linkage with the quantitative trait BMI was observed ($P=0.06$). Modeling linkage and association simultaneously resulted in no residual evidence for linkage at this haplotype marker ($P=0.57$). This indicated that the evidence of linkage at this site was accounted for by association; that is, the haplotype marker contained the disease mutation itself or was in strong LD with it.

General Population Data: Association of SNPs and Haplotypes with Obesity and BMI.

An association analysis in an independent sample of the general population was next performed (MONICA Augsburg LVH substudy). Results of the association of the five SNPs are summarized in Table 4 (FIG. 4) for the entire study sample as well as for matched case and control subjects. Odds ratios were calculated for the comparison of allele frequencies and the "homozygous trait" and "allele positivity" comparisons. Overall, the five SNPs consistently showed nominally significant association with obesity in all three comparisons, in both the entire study sample and the matched case and control subjects (entire study sample, best $P=0.0000$; matched sample, best $P=0.0007$ for rs863441). When the result was corrected for multiple testing for SNPs in LD, most P values remained significant. In the entire study sample, the increased risk presented by the presence of the minor allele of these SNPs ranged between 41 (P 0.014) and 56% ($P=0.001$).

Figure 3:
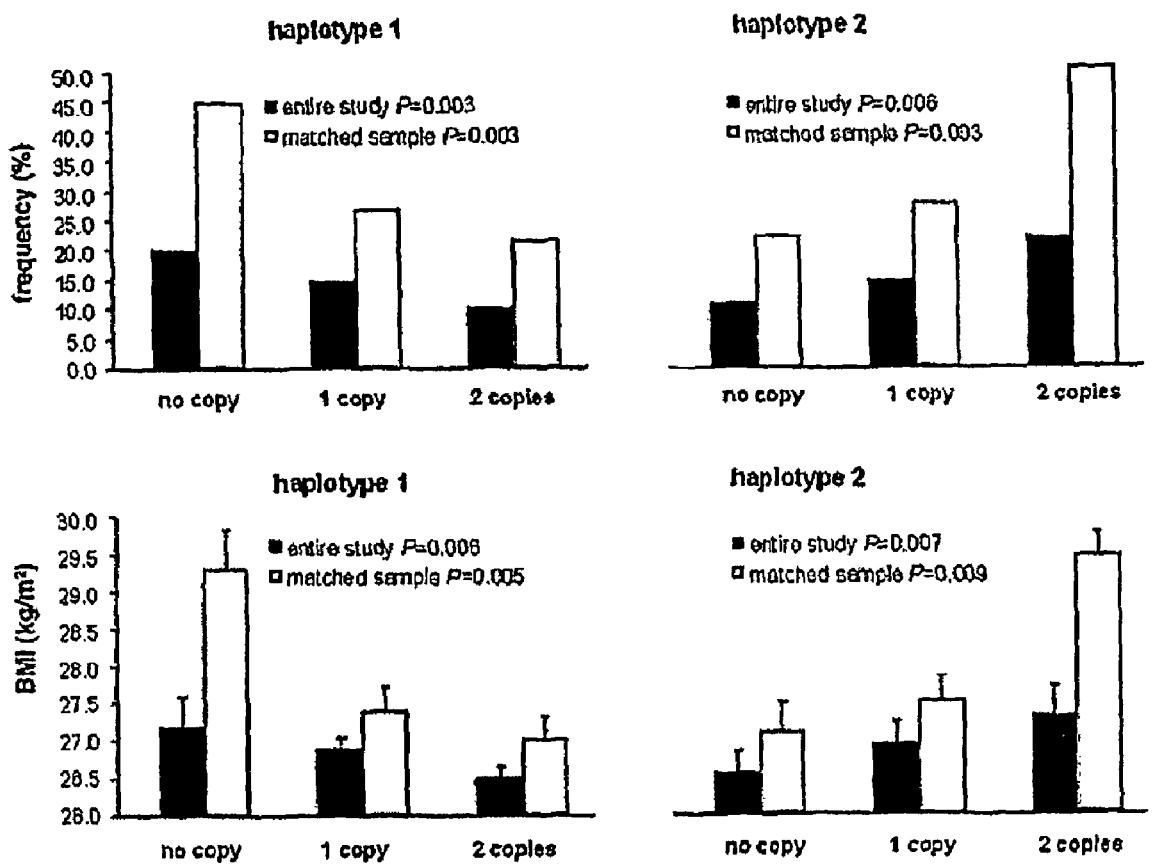
FIG. 3 shows the association of the number of copies of haplotypes 1 and 2 with obesity.

To further test for association, full haplotype analysis was performed. In agreement with the family data, haplotype 1 was more frequently present in non-obese individuals ("nonsusceptible," $P=0.002$ after 50,000 permutations) and haplotype 2 was more frequently found in obese individuals ("susceptible," $P=0.001$ after 50,000 permutations) (Table 3). A significant relation was observed between the number of copies of haplotypes 1 and 2 with the qualitative trait obesity in matched case and control subjects and that in the entire study sample. Individuals homozygous for the "susceptible" haplotype 2 or lacking the "nonsusceptible" haplotype 1 presented more often with obesity than individuals with one or no copy of the respective haplotype (haplotype 2: $P=0.003$ in the matched sample, $P=0.006$ in the entire sample; haplotype 1: $P=0.003$ in the matched sample, $P=0.003$ in the entire sample after 50,000 permutations) (FIG. 3). When tested for association with BMI, individuals carrying two copies of the "susceptible" haplotype 2 or no copy of the "nonsusceptible" haplotype 1 analogously presented with higher BMI than individuals with one or no copy of the respective haplotype (haplotype 2: $P=0.009$ in the matched sample, $P=0.007$ in the entire sample; haplotype 1: $P=0.005$ in the matched sample, $P=0.006$ in the entire sample after 50,000 permutations) (FIG. 3). The MONICA LVH population was divided into quartiles of BMI distribution and a significantly increasing frequency of the "susceptible" haplotype 2 was observed, from 23% in the lowest quartile to 30% in the highest quartile ($P<0.004$ for trend).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of predicting an increased susceptibility to obesity in a human subject, comprising
   a) providing a sample from the human subject,
   b) determining said subject's growth hormone secretagogue receptor (GHSR) haplotype at rs509035, rs572169, rs519384, rs512692 and rs863441 and,
   c) identifying the subject as having an increased susceptibility to obesity when rs509035A, rs572169A, rs519384A, rs512692T and rs863441C is detected.

2. A method of predicting a decreased susceptibility to obesity in a human subject, comprising
   a) providing a sample from the human subject,
   b) determining said subject's growth hormone secretagogue receptor (GHSR) haplotype at rs509035, rs572169, rs519384, rs512692 and rs863441 and,
   c) identifying the subject as having a decreased susceptibility to obesity when rs509035G, rs572169G, rs519384T, rs512692A and rs863441G is detected.

3. The method of claim 1 or 2, wherein said determining said subject's GHSR haplotype comprises a nucleic acid based detection assay.

4. The method of claim 3, wherein said nucleic acid based detection assay is selected from the group consisting of a sequencing assay and hybridization assay.

5. The method of claim 4, wherein said hybridization assay in an INVADER assay.

6. The method of claim 1 or 2, wherein said subject is not obese.

* * * * *